(12) United States Patent
Milis et al.

(10) Patent No.: US 11,766,464 B2
(45) Date of Patent: Sep. 26, 2023

(54) METHOD FOR GUT MUCOSA PREPARATION TO ENHANCE MICROBIAL ENGRAFTMENT

(71) Applicants: Antony Milis, Sydney (AU); Thomas Julius Borody, Five Dock (AU)

(72) Inventors: Antony Milis, Sydney (AU); Thomas Julius Borody, Five Dock (AU)

(*) Notice: Subject to any disclaimer, the term of this patent is extended or adjusted under 35 U.S.C. 154(b) by 0 days.

(21) Appl. No.: 17/616,591

(22) PCT Filed: Jul. 13, 2020

(86) PCT No.: PCT/AU2020/050724
§ 371 (c)(1),
(2) Date: Dec. 3, 2021

(87) PCT Pub. No.: WO2021/003535
PCT Pub. Date: Jan. 14, 2021

(65) Prior Publication Data
US 2022/0226399 A1      Jul. 21, 2022

Related U.S. Application Data

(60) Provisional application No. 62/873,032, filed on Jul. 11, 2019.

(51) Int. Cl.
*A61K 35/741* (2015.01)
*A61K 31/198* (2006.01)
*A61K 33/18* (2006.01)

(52) U.S. Cl.
CPC .......... *A61K 35/741* (2013.01); *A61K 31/198* (2013.01); *A61K 33/18* (2013.01)

(58) Field of Classification Search
CPC .................................................. A61K 35/741
See application file for complete search history.

(56) References Cited

FOREIGN PATENT DOCUMENTS

| WO | 2014078911 A1 | 5/2014 |
|---|---|---|
| WO | 2016183577 A1 | 11/2016 |
| WO | 2016191356 A1 | 12/2016 |
| WO | 2017210428 A1 | 12/2017 |
| WO | 2017218681 A1 | 12/2017 |
| WO | 2018006088 A1 | 1/2018 |

OTHER PUBLICATIONS

Borody et al., "Fecal microbiota transplantation: indications, methods, evidence, and future directions," Curr Gastroenterol Rep 15: 337, 7 pp., 2013.*
Chumppitazi et al. "Soad suds enema are efficacious and safe for treating fecal impaction in children with abdominal pain" Journal of Pediatric Gastroenterology Nutrition, 2016, v 63, n 1.
Gotter et al., "How to use a soap suds enema" Healthline, 2018.
Borody et al., "Fecal microbiota transplantation: indications, methods, evidence, and future directions" Curr Gastroenterol Rep. 2013.

* cited by examiner

*Primary Examiner* — Rosanne Kosson
(74) *Attorney, Agent, or Firm* — Greer, Burns & Crain, LTD.; Gregory P. Einhorn

(57) ABSTRACT

In alternative embodiments, provided are products of manufacture for microbiome transplantation and engraftment, including fecal microbiota transplantation (FMT) delivery devices, and methods for using them, including methods for replacing an individual's gastrointestinal (GI), e.g., colonic, microbiome, and methods for the treatment, amelioration or prevention of an in situ microbiome space, or a gastrointestinal (GI) disease, infection or condition or a disease or condition caused by, initiated by or exacerbated by a pathological microbiome, e.g., pathological GI or colonic microbiome. In particular a method for microbiome transplantation and engraftment in an individual in need thereof, the method comprising: removing of some or all colonic fecal material from the colon of the individual in need thereof by washing out colonic fecal material from the colon, wherein said washing out comprises administering a formulation comprising a biofilm dissolving or disrupting agent to the colon, and administering a FMT material, liquid, formulation or solution, or a normal microbiome, to the individual in need thereof.

16 Claims, No Drawings

METHOD FOR GUT MUCOSA PREPARATION TO ENHANCE MICROBIAL ENGRAFTMENT

This application is a national phase application claiming benefit of priority under 35 U.S.C. § 371 to Patent Convention Treaty (PCT) International Application serial number PCT/AU2020/050724, filed Jul. 13, 2020, now pending, which claims the benefit of priority to U.S. patent application serial number (USSN) 62/873,032, filed 11 Jul. 2019, the aforementioned applications are expressly incorporated herein by reference in their entirety and for all purposes.

FIELD

This invention generally relates to gastroenterology and colonic microbiome biology and engraftment. In alternative embodiments, provided are products of manufacture for microbiome transplantation and engraftment, including fecal microbiota transplantation (FMT) delivery devices, and methods for using them, including methods for replacing an individual's gastrointestinal (GI), e.g., colonic, microbiome, and methods for the treatment, amelioration or prevention of an in situ microbiome space, or a gastrointestinal (GI) disease, infection or condition or a disease or condition caused by, initiated by or exacerbated by a pathological microbiome, e.g., pathological GI or colonic microbiome.

BACKGROUND

Faecal (Fecal) Microbiota Transplantation (FMT) has a long history going back to the 4$^{th}$ century in China and consists of the introduction of healthy donor colonic microbiota into the gastrointestinal (GI) tract of a person with an abnormal microbiota and clinical illness. Current methodology introducing microbiota into the bowel uses trans-colonoscopic or enema infusions, or otherwise delivery of FMT material to the small bowel through a long naso-jejunal delivery tube. Use of equipment or devices for 'colonic' delivery of FMT material has been described, for example, see Meron et al, U.S. Pat. No. 10,244,980.

Use of the FMT to treat Clostridioides difficile (Clostridia changed to Clostridioides by the Clinical and Laboratory Standards Institute (CLSI) in 2016) infection has been very successful, and this requires 1 or 2 enemas of human homogenized flora to achieve a 90% or even higher cure rate. A high level of engraftment has been demonstrated in such patients.

However, numerous conditions such as irritable bowel syndrome (IBS), ulcerative colitis (UC) and constipation are rarely cured by one or two or even multiple FMT GI infusions, where the introduced FMT appears to have difficulty in achieving engraftment.

By far the most difficult to cure with FMT appears to be constipation. Worldwide researchers are trying various methods of achieving implantation of fecal bacteria using multiple implantations or antibiotic pre-treatment, use of so-called "superdonors", or using various methods of modifying the composition of the implanting flora, but to no avail. The implantation is not being achieved anywhere across the world. No matter what is attempted even multiple enemas of human stool generally fail to reverse constipation in any more than 20-30% of patients, even in those whom weekly infusions have taken place for more than 6 months.

Similarly, when trying to treat IBS, chronic abdominal pain of unknown origin, autism, and ulcerative colitis (UC) even recurrent enemas of normal human stool in well-prepared bowel linings fail to cure the conditions. In a colitis study where 81 patients had FMT carried out 5 out of 7 days for 8 weeks only 2/81 patients were cured of UC in the long-term. Cure can mean both clinical and histological disappearance and absence of UC in patients off all therapies for more than about 12 or more months.

Similarly, when trying to treat IBS, chronic abdominal pain of unknown origin, autism, and ulcerative colitis (UC) even recurrent enemas of normal human stool in well-prepared bowel linings fail to cure the conditions. In a colitis study where 81 patients had FMT carried out 5 out of 7 days for 8 weeks only 2/81 patients were cured of UC in the long-term. Cure can mean both clinical and histological disappearance and absence of UC in patients off all therapies for more than about 12 or more months.

SUMMARY OF INVENTION

In a first aspect of the invention, there is provided a method for microbiome transplantation and engraftment in an individual in need thereof, the method comprising:
removing of some or all colonic fecal material from the colon of the individual in need thereof by washing out colonic fecal material from the colon, wherein said washing out comprises administering a formulation comprising a biofilm dissolving or disrupting agent to the colon, and
administering a fecal microbiota transplantation (FMT) material, liquid, formulation or solution, or a normal microbiome, to the individual in need thereof.

In some embodiments, removing of some, substantially all or all colonic fecal material and/or said administering a fecal microbiota transplantation (FMT) may be carried out using a device as described in U.S. Patent Application Publication serial no. US/2018/0235448 A1; U.S. Patent Application Publication serial no. US/2018/0344907 A1; U.S. Pat. Nos. 10,022,488; 10,080,487; 10,179,202; 10,265,461; 10,322,226; and/or 9,949,618.

In some embodiments, the fecal microbiota transplantation (FMT) material, liquid, formulation or solution, or a normal microbiome, may be administered to the individual in need thereof less than 1 hour after the removing of some, substantially all or all of the colonic fecal material. In some embodiments, the fecal microbiota transplantation (FMT) material, liquid, formulation or solution, or a normal microbiome, may be administered to the individual in need thereof less than 15 minutes after the removing of some, substantially all or all of the colonic fecal material.

In some embodiments, the biofilm dissolving or disrupting agent may be a solution of soap in water, or be selected from the group consisting of N-acetylcysteine, dispersin, ribonucleic-acid-III inhibiting peptide (RIP), Salvadora persica extracts, competence-stimulating peptide (CSP) patulin (PAT), penicillic acid (PA)/EDTA, cathelicidin-derived peptides, small lytic peptide PTP-7, nitric oxide, cys-2-decenoic acid, sodium nitroprusside, s-nitroso-1-glutathione (GSNfaO), s-nitroso-N-acetylpenicillamine (SNAP), chlorhexidine, povidone-iodine (PI), a nanoemulsion, a lytic bacteriophage, a lactoferrin, a xylitol hydrogel, a synthetic iron chelator, a cranberry component, a curcumin, acetyl-11-keto-boswellic acid (AKBA), a barley coffee (BC) component, silver nanoparticles, a probiotic (e.g., Bacillus), sinefungin, N-acetyl-cysteine, S-adenosylmethionine, S-adenosyl-homocysteine, a Delisea furanone, a N-sulfonyl homoserine lactone, iron salts, ionic silver salts, arsenicals, selenium, titanium dioxide, gallium nitrate, ethanol, hydrogen peroxide, hydrochloric acid, formaldehyde, luminal formalin in low concentrations, ozonated water, super-oxidized aqueous solution, nitrofurantoin, hexamine hippurate, potassium hydroxide, mercuric chloride, iodine, disodium EDTA, ozone insufflation, and a combination of selenium and gentamicin; or be selected from the group consisting of azithromycin, clarithromycin, gentamicin, vancomycin, rifaximin, rifabutin, rifampicin, streptomycin, erythromycin, roxithromycin, DEA-CP, bismuth thiols, bismuth subcitrate; bismuth subsalicylate; bismuth ethanondiothols, bismuth dimercaprol, bismuth dimercapropranol, secnidazole, nitazoxanide, furazolidone, nitroimidazoles, paromomycin, iodoquinol, doxycycline, norfloxacin, ciprofloxacin, levofloxacin, and neomycin. In some embodiments, the biofilm dissolving or disrupting agent may be selected from the group consisting of a solution of soap in water, iodine, and N-acetylcysteine. Preferably, the biofilm dissolving or disrupting agent may be a solution of soap in water.

In a second aspect of the invention, there is provided a method of treatment of treatment or prevention of a gastrointestinal (GI) disease initiated by or exacerbated by a pathological colonic microbiome in an individual in need thereof, the method comprising carrying out the method of the first aspect of the invention.

In some embodiments, the gastrointestinal (GI) disease initiated by or exacerbated by a pathological colonic microbiome may be constipation or ulcerative colitis. The gastrointestinal (GI) disease initiated by or exacerbated by a pathological colonic microbiome may be constipation. The gastrointestinal (GI) disease initiated by or exacerbated by a pathological colonic microbiome may be ulcerative colitis.

In alternative embodiments, provided are products of manufacture for microbiome transplantation and engraftment, including fecal microbiota transplantation (FMT) delivery devices, and methods for using them.

In alternative embodiments, provided are methods for:
 microbiome transplantation and engraftment,
 fecal microbiota transplantation (FMT),
 replacing an individual's gastrointestinal (GI) or colonic microbiome,
 the treatment, amelioration or prevention of an in situ microbiome space, or
 the treatment, amelioration or prevention of a gastrointestinal (GI) disease, infection or condition or a disease or condition caused by, initiated by or exacerbated by a pathological microbiome, or a pathological GI or colonic microbiome,
 the method comprising:
 administering a fecal microbiota transplantation (FMT) material, liquid, formulation or solution, or a normal microbiome, to an individual in need thereof, using a device as described herein,
 wherein optionally the device is a device or product of manufacture as described in U.S. Patent Application Publication serial no. US/2018/0235448 A1; U.S. Patent Application Publication serial no. US/2018/0344907 A1; U.S. Pat. Nos. 10,022,488; 10,080,487; 10,179,202; 10,265,461; 10,322,226; and/or U.S. Pat. No. 9,949,618.

In alternative embodiments of methods as provided herein:
 the fecal microbiota transplantation (FMT) material, liquid, formulation or solution, or a normal microbiome, is administered to the individual in need thereof after removing of some, substantially all or all of the colonic fecal material from the individual in need thereof,
 wherein optionally the fecal microbiota transplantation (FMT) material, liquid, formulation or solution, or a normal microbiome, is administered to the individual in need thereof immediately after the removing of some, substantially all or all of the colonic fecal material, or is administered to the individual in need thereof within between about 1 minute and 1 hour after the removing of some, substantially all or all of the colonic fecal material,
 wherein optionally the removing of some, substantially all or all of the colonic fecal material from the individual in need thereof comprises use of a device or product of manufacture as described in U.S. Patent Application Publication serial no. US/2018/0235448 A1; U.S. Patent Application Publication serial no. US/2018/0344907 A1; U.S. Pat. Nos. 10,022,488; 10,080,487; 10,179,202; 10,265,461; 10,322,226; and/or 9,949,618; and,
 the method further comprises administering a biofilm dissolving or disrupting agent to the individual in need thereof before, during and/or after removing of some, substantially all or all of the colonic fecal material from the individual in need thereof,
 wherein optionally the administering to the individual in need thereof the biofilm dissolving or disrupting agent comprises use of a device or product of manufacture as described in U.S. Patent Application Publication serial no. US/2018/0235448 A1; U.S. Patent Application Publication serial no. US/2018/0344907 A1; U.S. Pat. Nos. 10,022,488; 10,080,487; 10,179,202; 10,265,461; 10,322,226; and/or U.S. Pat. No. 9,949,618.

In alternative embodiments, provided are products of manufacture comprising or having contained therein a fecal microbiota transplantation (FMT) material, liquid, formulation or solution, or a normal microbiome, and/or a biofilm dissolving or disrupting agent,
 wherein the product of manufacture comprises a device as described in U.S. Patent Application Publication serial no. US/2018/0235448 A1; U.S. Patent Application Publication serial no. US/2018/0344907 A1; U.S. Pat. Nos. 10,022,488; 10,080,487; 10,179,202; 10,265,461; 10,322,226; and/or 9,949,618.

In alternative embodiments, provided are uses of products of manufacture as provided herein, for:
 microbiome transplantation and engraftment,
 fecal microbiota transplantation (FMT),
 replacing an individual's gastrointestinal (GI) or colonic microbiome,
 the treatment, amelioration or prevention of an in situ microbiome space, or
 the treatment, amelioration or prevention of a gastrointestinal (GI) disease, infection or condition or a disease or condition caused by, initiated by or exacerbated by a pathological microbiome, or a pathological GI or colonic microbiome.

The details of one or more exemplary embodiments of the invention are set forth in the accompanying description below. Other features, objects, and advantages of the invention will be apparent from the description, and from the claims.

All publications, patents, patent applications cited herein are hereby expressly incorporated by reference for all purposes in their entirety.

DESCRIPTION OF EMBODIMENTS

The inventors have surprisingly found that washing the colon, and in particular removal of biofilm from the colon, prior to FMT, results in substantially improved microbial engraftment. Improved microbial engraftment after FMT in turn results in improved clinical outcomes.

In alternative embodiments, provided are products of manufacture for microbiome transplantation and engraftment, including fecal microbiota transplantation (FMT) delivery devices, and methods for using them.

In alternative embodiments, provided are methods for replacing an individual's gastrointestinal (GI), e.g., colonic, microbiome. In alternative embodiments, provided are methods for the treatment, amelioration or prevention of an in situ microbiome space, or a gastrointestinal (GI) disease, infection or condition or a disease or condition caused by, initiated by or exacerbated by a pathological microbiome, e.g., pathological GI or colonic microbiome.

The devices described herein utilize washing fluids for removing fecal matter from the colon. Specifically, the washing fluid may be administered to the colon of an individual in need thereof by means of the device to assist in removing fecal matter from the colon. The inventors have surprisingly found that including biofilm removing or biofilm dissolving agents or compounds in the washing fluid aids in removal of biofilm from the colon, thus improving microbial engraftment after FMT.

In alternative embodiments, provided are methods for replacing an individual's gastrointestinal (GI), e.g., colonic, microbiome, comprising use of a device as described in U.S. Patent Application Publication serial no. US/2018/0235448 A1, wherein in alternative embodiments the methods comprise cleansing substantially all or part of an individual's gastrointestinal (GI), e.g., a colon, of fecal matter or existing or in situ microbiome-comprising material using this device, followed by insertion or implantation of a microbiota, e.g., a fecal microbiota transplantation, or FMT, or a cultured synthetic microbiota, or a mixture thereof, using this device and/or another device, e.g., a device as described herein.

For example, in alternative embodiments, the device comprises a sleeve assembly for coupling a colonoscope insertion tube to an add-on tube, which can initially include washing material, following by FMT comprising materials, formulations or solutions. In alternative embodiments, the sleeve assembly defines an elongated lumen and comprises an inner sleeve sized to receive an insertion tube of a colonoscope, an outer sleeve encircling the inner sleeve, and one or more add-on tubes positioned between the inner sleeve and the outer sleeve, where the add-on tubes can initially include washing material, following by FMT comprising materials, formulations or solutions. The at least the inner sleeve can be collapsible to fit tightly over a colonoscope insertion tube received within the inner sleeve. The inner sleeve can be coupled to the outer sleeve at one or more locations along the length of the inner sleeve so that collapsing of the inner sleeve brings the outer sleeve radially closer to the inner sleeve, approximating the one or more add-on tubes to a colonoscope insertion tube received within the inner sleeve. In alternative embodiments, the same or a different colonoscope insertion tube or one or more add-on tubes are used to administer the FMT material or solutions.

In alternative embodiments, provided are methods for replacing an individual's gastrointestinal (GI), e.g., colonic, microbiome, comprising use of a device as described in U.S. Patent Application Publication serial no. US/2018/0344907 A1, wherein in alternative embodiments the methods comprise cleansing substantially all or part of an individual's gastrointestinal (GI), e.g., a colon, of fecal matter or existing or in situ microbiome-comprising material using this device, followed by insertion or implantation of a microbiota, e.g., a fecal microbiota transplantation, or FMT, or a cultured synthetic microbiota, or a mixture thereof, using this device and/or another device, e.g., a device as described herein.

For example, in alternative embodiments, the device is a colon cleaning device comprising: a tube through which liquid and fecal matter are removed from a colon of a patient, the tube having a longitudinal axis; a cleaning head positioned at the distal end of the tube, the cleaning head having at least one opening coaxial with the longitudinal axis, the at least one opening sized for fecal matter to enter the interior of the cleaning head from the colon; at least one disassembly element disposed within the cleaning head; and an actuating mechanism which actuates the disassembly element to perform sweeping displacement inside the cleaning head so that the at least one disassembly element rotates around the longitudinal axis to slice through the fecal matter; wherein the cleaning head and the tube are sized and shaped to be displaced along the colon of a patient. In alternative embodiments, the same or additional tube or tubes are used to administer the FMT material or solution after all or substantially most of the colonic fecal matter is removed by the device.

In alternative embodiments, provided are methods for replacing an individual's gastrointestinal (GI), e.g., colonic, microbiome, comprising use of a device as described in U.S. Pat. No. 10,022,488, wherein in alternative embodiments the methods comprise cleansing substantially all or part of an individual's gastrointestinal (GI), e.g., a colon, of fecal matter or existing or in situ microbiome-comprising material using this device, followed by insertion or implantation of a microbiota, e.g., a fecal microbiota transplantation, or FMT, or a cultured synthetic microbiota, or a mixture thereof, using this device and/or another device, e.g., a device as described herein.

For example, in alternative embodiments, the device is a colon cleaning device comprising: an evacuation conduit configured for maneuverability through the curves of the colon and for transporting material from the colon out of a body, the evacuation conduit being sized for insertion to transport the material from at least 1 meter into the colon and having a lateral aperture located at or near the distal end of the evacuation conduit, the lateral aperture being configured for positioning inside the colon to receive the evacuated material for the transporting upon suction being applied through the lateral aperture; and a source of fluid positioned on and external to the device and aimed at least one opening of the evacuation conduit, the source of fluid configured to a) irrigate with a jet aimed distally along an exterior of the device towards and across the aperture; and b) reach a position of material blocking the aperture with a jet strength strong enough to displace from the aperture pieces of the material moved to the aperture by suction inside the colon cleaning device; wherein the jet being activated to remove the blocking material in response to changes in pressure inside the evacuation conduit. In alternative embodiments, after washing of the colon, and remove of fecal material, a pipe and/or tube is inserted in the device (e.g., into the length of the device) to administer the FMT material or solution, or additional or different pipe(s) and/or tube(s) are used to administer the FMT material or solution.

In alternative embodiments, provided are methods for replacing an individual's gastrointestinal (GI), e.g., colonic, microbiome, comprising use of a device as described in U.S. Pat. No. 10,080,487, wherein in alternative embodiments the methods comprise cleansing substantially all or part of an individual's gastrointestinal (GI), e.g., a colon, of fecal matter or existing or in situ microbiome-comprising material using this device, followed by insertion or implantation of a microbiota, e.g., a fecal microbiota transplantation, or FMT, or a cultured synthetic microbiota, or a mixture thereof, using this device and/or another device, e.g., a device as described herein.

For example, in alternative embodiments, the device is an endoscopic device insertable into a body cavity, comprising: an element having a hollow body comprising a wall and an opening, the opening being open to the body cavity when the hollow body is inserted to the body cavity; a vacuum pump and a compressor; a tube configured for providing alternating vacuum and pressure to the opening of the hollow body from the vacuum pump and compressor (optionally regulated at 10 to 15 psi, or pounds per square inch), respectively, wherein the opening is configured to adhere to a wall of a colon under suction generated by the pump; electronic circuitry, configured to automatically alternate the alternating vacuum and pressure provided by the tube from the vacuum pump and compressor; a cleaning mechanism configured for removing solid and liquid matter from the hollow body using the suction, the cleaning mechanism including a pipe introduced at one end into the interior of the element, the other end introduced into a vessel, the pipe configured for supplying washing liquid from a liquid reservoir to the hollow body, the pipe and tube arranged longitudinally along the endoscope each terminating separately at a corresponding aperture in the hollow body wall; a convex element comprising a convex portion extending over, bulging convexly outward from, and dividing the opening; the tube additionally configured to allow removal of solid and liquid matter together with the washing liquid from the hollow body by the suction. In alternative embodiments, after washing of the colon, and remove of fecal material, the pipe and/or tube is also used to administer the FMT material or solution, or additional or different pipe(s) and/or tube(s) are used to administer the FMT material or solution.

In alternative embodiments, provided are methods for replacing an individual's gastrointestinal (GI), e.g., colonic, microbiome, comprising use of a device or system as described in U.S. Pat. No. 10,179,202, wherein in alternative embodiments the methods comprise cleansing substantially all or part of an individual's gastrointestinal (GI), e.g., a colon, of fecal matter or existing or in situ microbiome-comprising material using this device, followed by insertion or implantation of a microbiota, e.g., a fecal microbiota transplantation, or FMT, or a cultured synthetic microbiota, or a mixture thereof, using this device and/or another device, e.g., a device as described herein.

For example, in alternative embodiments, the device comprises a system for colonic cleaning comprising: a colon insertion tube having a body sized for insertion and cleaning up to a cecum of a colon; and an envelope that collects exhausted matter from the colon comprising: a body including a fecal container of at least 2 liters volumes, a distal flexible portion adapted to couple to the body of the colon insertion tube, and a proximal flexible portion having a seal adapted to seal to the colon insertion tube; and wherein a portion of the envelope extends over the colon insertion tube between the distal flexible portion and the proximal flexible portion, and is axially extendible and contractible so as to change length according to an insertion depth of the colon insertion tube, by movement of the seal along with the colon insertion tube as the insertion depth changes. In alternative embodiments, after washing of the colon, and remove of fecal material, the colon insertion tube is also used to administer the FMT material or solution, or additional or different colon insertion tubes, pipe(s) and/or tube(s) are used to administer the FMT material or solution.

In alternative embodiments, provided are methods for replacing an individual's gastrointestinal (GI), e.g., colonic, microbiome, comprising use of a device or system as described in U.S. Pat. No. 10,265,461, wherein in alternative embodiments the methods comprise cleansing substantially all or part of an individual's gastrointestinal (GI), e.g., a colon, of fecal matter or existing or in situ microbiome-comprising material using this device, followed by insertion or implantation of a microbiota, e.g., a fecal microbiota transplantation, or FMT, or a cultured synthetic microbiota, or a mixture thereof, using this device and/or another device, e.g., a device as described herein.

For example, in alternative embodiments, the device comprises a system for cleaning an intestine, comprising: an evacuation lumen for evacuating irrigation fluid from the intestine; a pressure source; at least one sensor, positioned to detect an environmental condition in or near the evacuation lumen; and a controller configured to: measure a flow status of the evacuation lumen based on reporting from the at least one sensor, determine that the flow status indicates incipient blockage before the incipient blockage amounts to more than a 40% impairment of flow, and adjust the pressure from the pressure source to prevent the incipient blockage from increasing, based on the determination; wherein the being configured to determine that the flow status indicates incipient blockage comprises being configured to determine a location in the system of the incipient blockage, the location being a basis on which the pressure is adjusted. The pressure source can be operable to alternately apply proximally-directed and distally-directed pressure gradients to the evacuation lumen. comprises a plurality of evacuation lumens; and the pressure applied to each of the plurality of evacuation lumens by the pressure source can be individually controllable. In alternative embodiments, after washing of the colon, and remove of fecal material, the device (e.g., the evacuation lumen) is also used to administer the FMT material or solution, or additional or different devices are used to administer the FMT material or solution.

In alternative embodiments, provided are methods for replacing an individual's gastrointestinal (GI), e.g., colonic, microbiome, comprising use of a device or system as described in U.S. Pat. No. 10,322,226, wherein in alternative embodiments the methods comprise cleansing substantially all or part of an individual's gastrointestinal (GI), e.g., a colon, of fecal matter or existing or in situ microbiome-comprising material using this device, followed by insertion or implantation of a microbiota, e.g., a fecal microbiota transplantation, or FMT, or a cultured synthetic microbiota, or a mixture thereof, using this device and/or another device, e.g., a device as described herein.

For example, in alternative embodiments, the device comprises a channel for evacuating fecal waste from a human colon, comprising: a lumen, sized for insertion of a distal end thereof to a distal end of the colon; the lumen having a lobed cross-section comprising at least a first and second lobe; a passage between the first and second lobes comprising at least one slot narrower than the widest extent of the cross-section of the first lobe; the first lobe having a cross-sectional area at least 4 times larger than the cross-sectional area of the second lobe; and wherein fluid between the first and second lobe is gated by a one-way valve member extending along the slot. The channel can be enclosed by a wall constructed to resist collapse under application of a pressure differential of at least 0.2 Atm lower within the lumen than surrounding pressure. The evacuating can be through at least one intake aperture of an evacuation lumen, the predetermined size is determined by exclusion of the particles from the evacuation lumen, and the predetermined size is smaller than the largest of the at least one intake apertures. In alternative embodiments, the device comprise a channel for evacuating fecal waste from a human colon comprising: a lumen, sized for insertion of a distal end thereof to a distal end of the colon; wherein external access into the lumen at the distal end of the lumen is through at least one aperture; and the at least one aperture is configurable from among a plurality of different sizes. In alternative embodiments, after washing of the colon, and remove of fecal material, the device is also used to administer the FMT material or solution, or additional or different devices, tubes, pipe(s) and/or tube(s) are used to administer the FMT material or solution.

In alternative embodiments, provided are methods for replacing an individual's gastrointestinal (GI), e.g., colonic, microbiome, comprising use of a device or system as described in U.S. Pat. No. 9,949,618, wherein in alternative embodiments the methods comprise cleansing substantially all or part of an individual's gastrointestinal (GI), e.g., a colon, of fecal matter or existing or in situ microbiome-comprising material using this device, followed by insertion or implantation of a microbiota, e.g., a fecal microbiota transplantation, or FMT, or a cultured synthetic microbiota, or a mixture thereof, using this device and/or another device, e.g., a device as described herein.

For example, in alternative embodiments, the device comprises a sleeve assembly for coupling a colonoscope insertion tube to an add-on tube. In alternative embodiments, the sleeve assembly defines an elongated lumen and comprises an inner sleeve sized to receive an insertion tube of a colonoscope, an outer sleeve encircling the inner sleeve, and one or more add-on tubes positioned between the inner sleeve and the outer sleeve. In alternative embodiments, at least the inner sleeve is collapsible to fit tightly over a colonoscope insertion tube received within the inner sleeve. In some embodiments, the inner sleeve is coupled to the outer sleeve at one or more locations along the length of the inner sleeve so that collapsing of the inner sleeve brings the outer sleeve radially closer to the inner sleeve, approximating the one or more add-on tubes to a colonoscope insertion tube received within the inner sleeve. In alternative embodiments, the device comprises a sleeve assembly for coupling between an endoscope insertion tube and one or more add-on tubes, the sleeve assembly comprising: an inner sleeve defining an elongated lumen with an open end, and having: in a relaxed collapsed state, an inner sleeve diameter smaller than a diameter of an endoscope insertion tube inserted therein, and an expanded state sized to surroundingly receive at least 70% of a length of the endoscope insertion tube arranged longitudinally within the inner sleeve; an elastic outer sleeve encircling the inner sleeve; and one or more add-on tubes extending longitudinally between the inner sleeve and the outer sleeve; wherein the inner sleeve and the outer sleeve have the same elasticity and define between them an intermediate lumen, wherein the intermediate lumen is: sealed at one end by a proximal housing and at the other end by a distal housing, and at least partially air-filled; wherein expansion of the inner sleeve expands the outer sleeve; and wherein the inner sleeve is collapsible from the expanded state to the endoscope insertion tube diameter to fit tightly over the received length of the endoscope insertion tube; and wherein the inner sleeve is attachingly fixed to the outer sleeve at one or more locations along the inner sleeve, and collapse of the inner sleeve from the expanded state redistributes the air in the lumen and brings about collapse of the outer sleeve radially closer to the endoscope insertion tube, and brings the one or more add-on tubes closer to the endoscope insertion tube. In alternative embodiments, after washing of the colon, and remove of fecal material, the device is also used to administer the FMT material or solution, or additional or different devices or colonoscope insertion tube(s) are used to administer the FMT material or solution.

Fecal Microbiota Transplantation (FMT)

In alternative embodiments, products of manufacture and methods as provided herein comprise use and/or administration of a fecal microbiota transplantation, or FMT, or FMT material, solutions or formulations. In alternative embodiments, following treatments using devices as provided herein, for example, after a colon is washed and all or substantially most fecal matter is removed, FMT is carried out (is administered), e.g., once or twice or can be continued for a number of days or weeks or until such time the newly infused FMT material has the desired effect, e.g., treating, preventing or ameliorating (including lessening the symptoms of, or delaying the progression of) a target disease, illness, infection or condition.

In alternative embodiments, the FMT and the FMT procedure can comprise any FMT composition or procedure known in the art, for example, as described in U.S. Pat. Nos: 10,251,914; 10,226,431; 10,220,089; 10,064,900; 10,064,899; 10,028,980; 10,058,576; 9,623,056; 9,610,308; 9,572,842; 9,468,658; 9,408,872; 9,320,763; 9,308,226; 9,192,361.

Preferably, the FMT may be administered immediately after the removing of some, substantially all or all of the colonic fecal material. The FMT may be administered to the individual in need thereof within between about 1 minute and 1 hour after the removing of some, substantially all or all of the colonic fecal material. The FMT may be administered to the individual in need thereof less than 1 hour after the removing of some, substantially all or all of the colonic fecal material. The FMT may be administered to the individual in need thereof less than 15 minutes after the removing of some, substantially all or all of the colonic fecal material. The FMT may be administered to the individual in need thereof less than 5 minutes after the removing of some, substantially all or all of the colonic fecal material. The FMT may be administered to the individual in need thereof less than 1 minute after the removing of some, substantially all or all of the colonic fecal material.

In alternative embodiments, the FMT comprises or contains therein stool material, for example: lyophilized stool; fresh liquefied stool; frozen stool which has been thawed out; pre-filtered stool with or without spiked (or added) bacteria, such as beneficial probiotics, for example, probiotics comprising a *Faecalibacterium* such as *Faecalibacterium prausnitzii;* and/or re-suspended, cultured or liquid lyophilized bacteria or spores. In alternative embodiments, the FMT comprises or contains therein lyophilized stool suspended in water or saline with or without a spiked (or added) bacteria. In alternative embodiments, the FMT comprises or contains therein ultra-filtered material, where the ultra-filtration removes substantially most of the bacteria and fungi but leaves behind viruses and bacteriophages. In alternative embodiments, the FMT comprises or contains therein re-suspended, cultured or liquid lyophilized bacteria or spores with or without spiked (added) additional components such as drugs, probiotics or prebiotics.

The fecal microbiota transplantation (FMT) material, liquid, formulation or solution may contain stool material from a person who is not suffering from a gastrointestinal disease or disorder. The fecal microbiota transplantation (FMT) material, liquid, formulation or solution may contain a normal microbiome. A normal microbiome may be a microbiome obtained from a person who is not suffering from a gastrointestinal disease or disorder.

In alternative embodiments, the FMT comprises or contains therein a temperature sensitive polymer such as thermogel™ or equivalent, which when mixed with a fecal microbiota or another bacterium, which is a liquid at room temperature but gels solidifies when it reaches or is near body temperature (for example, gels at about 37° C.).

In alternative embodiments, the total volume of the FMT material is between about 300 ml to 1000 ml, 100 ml to 2000 ml, or 50 ml to 3000 ml.

Biofilm Removing or Disrupting Agents and Compounds

In alternative embodiments, products of manufacture and methods as provided herein comprise use of biofilm removing or biofilm dissolving agents or compounds, or other agents or compositions, for example, therapeutic compositions. In alternative embodiments, biofilm removing or biofilm dissolving agents or compounds, or other agents or compositions are applied using devices as described herein before administration of the FMT materials, formulations or solutions. Specifically, the washing fluid utilized by devices as described herein may comprise biofilm removing or biofilm dissolving agents or compounds.

A biofilm dissolving or disrupting agent is an agent which is capable of dissolving or disrupting a biofilm.

A biofilm is an aggregate of microorganisms such as bacteria in which cells of the microorganism may be embedded within a self-produced matrix of extracellular polymeric substances (such as polysaccharides, proteins, lipids, and DNA) that adhere to each other and/or to a surface.

In alternative embodiments, in practicing the methods or uses as provided herein, biofilm disrupting or dissolving formulations or compounds are administered before or during (co-administered), or co-formulated with (e.g., in a liquid enema), or separately formulated, as an administered formulation for washing out colonic fecal material. In alternative embodiments, these formulation can disrupt or remove biofilms, and alternatively are used to separate biofilm from GI mucosa, including colonic mucosa, including removing adherent the adherent polysaccharide/DNA—containing layer, the so-called "biofilm".

In alternative embodiments, products of manufacture and methods as provided herein comprise use of biofilm removing formulations comprising a soap, wherein alternatively the biofilm removing formulations comprising a soap in a liquid comprising an aqueous saline, super-oxidized aqueous solution, pH neutral Ringer's Lactate (Hartmann's) or water solution, wherein optionally the water can be tap water, distilled water, ozonated water, alkaline water or any mixture thereof. The soap may be a vegetable oil-derived soap such as Castile soap. In alternative embodiments, a device as described herein is used to deliver the biofilm disrupting or removing formulation or agent before administration of the FMT materials, formulations or liquids, and the biofilm disrupting or removing formulation or agent can be administered with or after administration of solutions to remove colonic fecal matter, e.g., using a device as described herein.

In alternative embodiments, biofilm disrupting components or agents are administered before, during (for example, concurrent with) and/or after the administration of a colonic wash formulation, e.g., as lozenges, dissolvable wafers, strip or patches, lollies (e.g., lollypops, "pops" or suckers), candies, gums (e.g., chewing gums), aerosols, powders and sprays. In alternative embodiments, biofilm disrupting agents are administered either before colonic wash treatment and/or during and/or after treatment with a therapeutic combination or composition. In alternative embodiments, biofilm disrupting agents are used singly or in combination.

In alternative embodiments, biofilm disrupting agents comprise one or more enzymes such as a proteinase, an amylase, a lipase, a deoxyribonuclease (DNase) such as dornase alpha, or PULMOZYME™, an alginase, a lyase, or a glycoside hydrolase such as dispersin B. DNases are effective in disrupting a biofilm matrix because some 30% of the biofilm is made up of DNA.

In alternative embodiments, biofilm disrupting agents that can be administered with formulations as described herein either as components of the formulation or administered separately, including for example, antibiotics such as: azithromycin, clarithromycin, gentamicin, vancomycin, rifaximin, rifabutin, rifampicin, streptomycin, erythromycin, roxithromycin, DEA-CP, bismuth thiols, bismuth subcitrate; bismuth subsalicylate; bismuth ethanondiothols, bismuth dimercaprol, bismuth dimercapropranol and other antibiotics, and combinations thereof. In alternative embodiments, biofilm disrupting agents that are administered with formulations as described herein or added to formulations as described herein include anti-parasite antimicrobial agents. In alternative embodiments, these biofilm disrupting agents are combined in dual, three-agent, or four or more agent combinations. In one embodiment, the antibiotic combination comprises: secnidazole, nitazoxanide and furazolidone. In one embodiment, the antibiotic combination comprises: nitroimidazoles, paromomycin, iodoquinol, doxycycline, norfloxacin, ciprofloxacin or levofloxacin, vancomycin, rifaximin, streptomycin or neomycin or any combination thereof.

In alternative embodiments, other biofilm degrading substances are used to practice formulations and methods as provided herein, including: N-acetylcysteine, dispersin, ribonucleic-acid-III inhibiting peptide (RIP), *Salvadora persica* extracts, competence-stimulating peptide (CSP) patulin (PAT), penicillic acid (PA)/EDTA, cathelicidin-derived peptides, small lytic peptide PTP-7 (see e.g., Kharidia (2011) J. Microbiol. 49(4):663-8, Epub 2011 Sep. 2), nitric oxide, cys-2-decenoic acid, sodium nitroprusside, s-nitroso-1-glutathione (GSNfaO), s-nitroso-N-acetylpenicillamine (SNAP), chlorhexidine, povidone-iodine (PI), a nanoemulsion, a lytic bacteriophage, a lactoferrin, a xylitol hydrogel, a synthetic iron chelator, a cranberry component, a curcumin, an acetyl-11-keto-boswellic acid (AKBA), a barley coffee (BC) component, a silver nanoparticle, silver nanoparticles, a probiotic (e.g., *Bacillus*), sinefungin, N-acetylcysteine, S-adenosylmethionine, S-adenosyl-homocysteine, a *Delisea* furanone, a N-sulfonyl homoserine lactone, iron or ionic silver salts (which can inhibit film formation, and permit antibiotics to be more active), arsenicals, selenium, titanium dioxide, gallium nitrate, an alcohol such as ethanol, hydrogen peroxide, hydrochloric acid, formaldehyde or luminal formalin in low concentrations, ozonated water, super-oxidized aqueous solution, nitrofurantoin (e.g., MACROBID™), hexamine hippurate (e.g., HIPREX™), potassium hydroxide, mercuric chloride, iodine and/or disodium EDTA. Ozone insufflations can also be used to disrupt the biofilm. In one embodiment, a combination of selenium and gentamicin is used to dissolve a biofilm.

In alternative embodiments, biofilm degrading substances are used to practice formulations and methods as provided herein comprise: a polyol, including xylitol, sorbitol, mannitol, erythritol, isomalt, maltitol syrup, lactitol, hydrogenated starch hydrolysates or combinations thereof.

In alternative embodiments, biofilm degrading substances are used to practice formulations and methods as provided herein comprise a surfactant, e.g., a biosurfactant, e.g., a biosurfactant extracted from a probiotic such as a *Bacillus* strains, including *Bacillus licheniformis*.

In alternative embodiments, a collection of maggots in a tea bag or bio-bag (e.g., as manufactured by Monarch Laboratories, Irvine Calif.) are used with methods as provided herein to remove the biofilm from wounds. Maggot secretions pass through the bio-bag or teabag walls and can disrupt and dissolve biofilms.

In alternative embodiments, anti-quorum sensing (QS) compounds and/or enzymes are used as biofilm disrupting components or agents, e.g., to block several cascading pathways of the resident microbes within the biofilm. QS compounds and/or enzymes that can be used or incorporated in formulations as provided herein include S-adenosylhomocysteine, sinefungin, a N-sulfonyl homoserine lactone and synthetic derivatives, as well as 'biofilm-eating' probiotics working on the QS mechanism. Biofilm disrupting probiotics that can be used or incorporated in formulations as provided herein include various *Bacillus* strains which secrete AiiA enzyme.

Prebiotics that can be used or incorporated in formulations as described herein include prebiotics from food; e.g., prebiotics can be used to pre-treat patients in methods as provided herein. Prebiotics that can be used or incorporated in formulations as provided herein include peas, tomato, rice and garlic or extracts thereof, where in alternative embodiments the prebiotics comprise substances affecting the QS.

Prebiotics and Probiotics

In alternative embodiments, methods as provided herein comprise administration of prebiotics and/or probiotics, and alternatively the prebiotics and/or probiotics can be administered before, with and/or after administration of the FMT materials, formulations or solutions.

Prebiotics that can be used in methods as provided herein include prebiotics from food; e.g., prebiotics can be used to pre-treat patients in methods as provided herein. Prebiotics that can be used or incorporated in formulations as provided herein include peas, tomato, rice and garlic or extracts thereof, where in alternative embodiments the prebiotics comprise substances affecting the QS. In alternative embodiments, prebiotics that can be used in methods as provided herein include oligosaccharides, e.g., as described in U.S. patent application publication no. 20190194239 A1, where the prebiotics can be prepared by mixing starch, cellulose and/or lignocellulosic biomass.

In alternative embodiments, prebiotics that can be used in methods as provided herein include oligosaccharides, e.g., as described in U.S. patent application publication no. 20190160114 A1, including fructo-oligosaccharides; beta-(2,6) oligofructans; inulins; beta-(2,1) oligofructans; beta-1,2 oligosaccharides terminated with glucose; beta-(1,2)-galactooligosaccharides; beta-(1,3)-galactooligosaccharides; beta-(1-4)-galactooligosaccharides; beta-(1,6) galactooligosaccharides; alpha-(1,2)-galactooligosaccharides; alpha-(1,3)-galactooligosaccharides; alpha-(1-4)-galactooligosa.ccharides, alpha-(1,6) galactooligosaccharides; beta-(1,4) xylooligosaccharides; alpha-(1,4) xylooligosaccharides; hemicelluloses; arabinoxylan; galactomannan; guar gum; acacia gum; arabinogalactan, pectin, amylopectin, or a combination thereof.

Prebiotics that can be used in methods as provided herein include any known probiotic. For example, in alternative embodiments methods as provided herein can comprise use of probiotics as described in U.S. patent application publication no. 20190192590 A1. In alternative embodiments, probiotics that can be used in methods as provided herein include viable bacteria, yeasts and other microorganisms, and combinations thereof; where the bacteria can be from or derived from the genus *Lactobacillus*, for example, including *Lactobacillus paracasei, Lactobacillus acidophilus, Lactobacillus amylolyticus, Lactobacillus amylovorus, Lactobacillus alimentarius, Lactobacillus aviaries, Lactobacillus brevis, Lactobacillus buchneri, Lactobacillus casei, Lactobacillus cellobiosus, Lactobacillus coryniformis, Lactobacillus crispatus, Lactobacillus curvatus, Lactobacillus delbrueckii, Lactobacillus farciminis, Lactobacillus fermentum, Lactobacillus gallinarum, Lactobacillus gasseri, Lactobacillus helveticus, Lactobacillus hilgardii, Lactobacillus johnsonii, Lactobacillus kefiranofaciens, Lactobacillus kefiri, Lactobacillus mucosae, Lactobacillus panis, Lactobacillus collinoides, Lactobacillus paraplantarum, Lactobacillus pentosus, Lactobacillus plantarum, Lactobacillus pontis, Lactobacillus reuteri, Lactobacillus rhamnosus, Lactobacillus sakei, Lactobacillus salivarius* and/or *Lactobacillus sanfranciscensis.*

In alternative embodiments methods as provided herein can comprise use of probiotics as described in U.S. patent application publication no. 20190183944 A1 or 20190137493 A1, including lactic acid-producing bacteria, or lactate utilizing, propionic acid producing bacteria from one or more *Cutibacteria* strains; or bacteria from or derived from the genus: *Prevotellaceae, Bifidobacteria, Lactobacilli, Lactococci, Streptococci, Enterococci, Leuconostoc* and/or *Weissella.*

In alternative embodiments methods as provided herein can comprise use of probiotics as described in U.S. patent application publication no. 20190160118 A1, including bacteria from or derived from the genus *Pediococcus, Dialister, Veillonella, Faecalibacterium, Phascolarctobacteria, Oscillospira, Ruminococcus, Bacteroides,* and/or *Blautia;* or from the family Christensenellaceae, and/or from the phylum cyanobacteria.

In alternative embodiments methods as provided herein can comprise use of probiotics as described in U.S. patent application publication no. 20190192587 A1, including the bacteria *Lactobacillus reuteri, Pediococcus acidilactici, Enterococcus faecium,* and/or *Pediococcus pentosaceus.*

Products of Manufacture

In alternative embodiments, provided are devices as described herein comprising FMT material or solution, or further comprising, or being operatively connected to or linked to, repositories or storage units or compartments containing therein FMT, formulations materials or solutions.

In alternative embodiments, the FMT materials, formulations or solutions are contained in removable repositories or storage units or compartments that can be removably attached to a device as described herein.

Any of the above aspects and embodiments can be combined with any other aspect or embodiment as disclosed here in the Summary and/or Detailed Description sections.

As used in this Specification and the appended claims, the singular forms "a," "an" and "the" include plural referents unless the context clearly dictates otherwise.

Unless specifically stated or obvious from context, as used herein, the term "or" is understood to be inclusive and covers both "or" and "and".

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

A number of embodiments of the invention have been described. Nevertheless, it can be understood that various modifications may be made without departing from the spirit and scope of the invention. Accordingly, other embodiments are within the scope of the following claims.

EXAMPLES

Example 1

A 42 year old patient with ulcerative colitis had been treated with anti-inflammatory agents until the calprotectin was recurrently at less than 15 micrograms/milligram. The patient was then invited to have her biofilm removed using a colonic washout device which was modified to deliver 8 litres through an open system speculum into the rectum. Such a volume could be repeatedly infused using different dissolving liquids. The patient had bowel preparation beforehand using Moviprep. She ceased all her antibiotic therapy but maintained anti-inflammatory agents such as Purinethol and Humira and then had continuous washing out of the bowel on the colonic washout machine. 8 litre cycles of 54 g of Vitamin C dissolved in saline was first infused followed by a washout with normal saline. The fluid would enter the rectum through the fine tube, run around the whole colon to the cecum and then start coming out beside the rectal tube. Once the 8 litres, followed by saline, were finished, she was then given 0.3% iodine in saline at a volume of 8 litres. After that, the saline at a volume of 4 litres was run in until all the iodine had come out. N-acetyl cysteine 3 g in saline was infused next, followed by saline and finally soap and water infusion followed by saline. Within 15 minutes of the biofilm washout the patient underwent trans-colonoscopic infusion of the faecal flora being infused initially into the cecum and then every 10 cm through to the sigmoid colon. After that infusion, the patient recovered from sedation, was given a further enema of faecal material into the colon. The patient responded very well with the colitis symptoms completely under control with good control continuing for 8 months follow up. She was able to stop the Humira and maintain on only 25 mg Purinethol for 4 months after which this was stopped, and only vitamin D 10 000 units per day was continued.

Example 2

A 65 year old male with an 18 year history of chronic constipation was previously treated with coloxyl and dulcolax, Vancomycin and Dipentum for 8 months until he was defecating well, was selected to undergo faecal transplantation. He was placed on a colonic washout machine (Aquanet, with an 'open system' speculum) able to infuse high volume of fluid after initially preparing the bowel with Moviprep. There was a number of biofilm-dissolving agents used. The first one that was used was Microdacyn at a volume of 4 litres, followed by saline and then followed by 54 g of Vitamin C using Plenvu. After that, soap and water was used. The patient emptied the bowel in the toilet, passing simply watery liquid without any brown suspended stool bits. The patient was then immediately given an enema of faecal transplant followed by a second enema an hour later. For the next 12 months from having used 10 Coloxyl per day and 2 Dulcolax, Movicol and Vancomycin, the patient was able to have 2 stools per day with fairly large well-formed stools with normal urge, even passing stools when travelling overseas—without any drugs. The preparation of the bowel by removing the biofilm was the crucial aspect of this treatment.

The invention claimed is:

1. A method for microbiome transplantation and engraftment in an individual in need thereof, the method comprising:
   (a) washing out colonic fecal material from the colon, wherein said washing out comprises administering in an effective amount a formulation comprising a biofilm dissolving or disrupting agent to or into the colon, wherein the biofilm dissolving or disrupting agent comprises one or more agents selected from the group consisting of: soap in water, iodine, N-acetylcysteine, dispersin, ribonucleic-acid-III inhibiting peptide (RIP), Salvadora persica extracts, competence-stimulating peptide (CSP) patulin (PAT), penicillic acid (PA)/EDTA, cathelicidin-derived peptides, small lytic peptide (PTP)-/7, nitric oxide, cys-2-decenoic acid, sodium nitroprusside, s-nitroso-1-glutathione (GSNfaO), s-nitroso-N-acetylpenicillamine (SNAP), chlorhexidine, povidone-iodine (PI), a nanoemulsion, a lytic bacteriophage, a lactoferrin, a xylitol hydrogel, a synthetic iron chelator, a cranberry component, curcumin, acetyl-11-keto-boswellic acid (AKBA), a barley coffee (BC) component, silver nanoparticles, sinefungin, S-adenosylmethionine, S-adenosyl-homocysteine, a Delisea furanone, an N-sulfonyl homoserine lactone, iron salts, ionic silver salts, arsenicals, selenium, titanium dioxide, gallium nitrate, ethanol, hydrogen peroxide, hydrochloric acid, formaldehyde, luminal formalin, ozonated water, super-oxidized aqueous solution, nitrofurantoin, hexamine hippurate, potassium hydroxide, mercuric chloride, iodine, disodium EDTA, a combination of selenium and gentamicin, and a combination thereof; and
   (b) after washing out the colonic fecal material from the colon, administering to the individual in a therapeutically effective amount:
     (i) a fecal microbiota transplantation (FMT) material, liquid, formulation or solution, or
     (ii) a material, liquid, formulation or solution comprising a normal microbiome.

2. The method of claim 1, wherein said removing of some, substantially all or all colonic fecal material and/or said administering a fecal microbiota transplantation (FMT) is carried out using a device as described in U.S. Patent Application Publication serial no. US/2018/0235448 A1; U.S. Patent Application Publication serial no. US/2018/0344907 A1; U.S. Pat. Nos. 10,022,488; 10,080,487; 10,179,202; 10,265,461; 10,322,226; and/or 9,949,618.

3. The method of claim 1, wherein the fecal microbiota transplantation (FMT) material, liquid, formulation or solution, or the material, liquid, formulation or solution comprising the normal microbiome, is administered to the individual in need thereof immediately after the removing of some, substantially all or all of the colonic fecal material.

4. The method of claim 1, wherein the fecal microbiota transplantation (FMT) material, liquid, formulation or solution, or the material, liquid, formulation or solution comprising the normal microbiome, is administered to the individual in need thereof less than 1 hour after the removing of some, substantially all or all of the colonic fecal material.

5. The method of claim 1, wherein the fecal microbiota transplantation (FMT) material, liquid, formulation or solution, or the material, liquid, formulation or solution comprising the normal microbiome, is administered to the individual in need thereof less than 15 minutes after the removing of some, substantially all or all of the colonic fecal material.

6. The method of claim 1, wherein the biofilm dissolving or disrupting agent further comprises a *Bacillus* sp.

7. The method of claim 1, wherein the formulation comprising the biofilm dissolving or disrupting agent further comprises a compound or composition selected from the group consisting of: azithromycin, clarithromycin, gentamicin, vancomycin, rifaximin, rifabutin, rifampicin, streptomycin, erythromycin, roxithromycin, DEA-CP, bismuth thiols, bismuth subcitrate; bismuth subsalicylate; bismuth ethanondiothols, bismuth dimercaprol, bismuth dimercapropranol, secnidazole, nitazoxanide, furazolidone, nitroimidazoles, paromomycin, iodoquinol, doxycycline, norfloxacin, ciprofloxacin, levofloxacin, neomycin and any combination thereof.

8. The method of claim 7, wherein the formulation comprising the biofilm dissolving or disrupting agent further comprises a solution of soap in water, iodine, and N-acetylcysteine.

9. The method of claim 1, wherein the formulation comprising the biofilm dissolving or disrupting agent further comprises N-acetylcysteine.

10. The method of claim 1, wherein the formulation comprising the biofilm dissolving or disrupting agent further comprises dispersin.

11. The method of claim 1, wherein the formulation comprising the biofilm dissolving or disrupting agent further comprises S-adenosyl-homocysteine.

12. The method of claim 1, wherein the formulation comprising the biofilm dissolving or disrupting agent further comprises ethanol.

13. The method of claim 1, wherein the formulation comprising the biofilm dissolving or disrupting agent further comprises hydrogen peroxide.

14. The method of claim 1, wherein the washing out of the colonic fecal material from the colon further comprises administering: an ozone insufflation, an ozonated water or a super-oxidized aqueous solution, or nitrofurantoin.

15. The method of claim 1, wherein the formulation comprising the biofilm dissolving or disrupting agent further comprises potassium hydroxide.

16. The method of claim 1, wherein the formulation comprising the biofilm dissolving or disrupting agent further comprises disodium EDTA.

* * * * *